US006759360B2

(12) United States Patent
Wang et al.

(10) Patent No.: US 6,759,360 B2
(45) Date of Patent: Jul. 6, 2004

(54) INTERIOR SURFACE MODIFICATIONS OF MOLECULAR SIEVES WITH ORGANOMETALLIC REAGENTS AND THE USE THEREOF FOR THE CONVERSION OF OXYGENATES TO OLEFINS

(75) Inventors: Kun Wang, Bridgewater, NJ (US); Guang Cao, Branchburg, NJ (US); Michael Joseph Brennan, Scotch Plains, NJ (US); Karl G. Strohmaier, Port Murray, NJ (US); Richard B. Hall, Whitehouse Station, NJ (US)

(73) Assignee: ExxonMobil Chemical Patent Inc., Houston, TX (US)

( * ) Notice: Subject to any disclaimer, the term of this patent is extended or adjusted under 35 U.S.C. 154(b) by 15 days.

(21) Appl. No.: 10/112,250

(22) Filed: Mar. 29, 2002

(65) Prior Publication Data

US 2003/0187313 A1 Oct. 2, 2003

(51) Int. Cl.[7] .................................................. B01J 29/85
(52) U.S. Cl. ................. 502/85; 423/326; 423/DIG. 30; 502/214
(58) Field of Search ................................. 423/713, 714, 423/715, 326, DIG. 30, 306; 502/85, 214, 60, 62

(56) References Cited

U.S. PATENT DOCUMENTS

| | | | |
|---|---|---|---|
| 3,258,455 A | 6/1966 | Natta et al. ................. 260/93.7 |
| 3,305,538 A | 2/1967 | Natta et al. ................. 260/93.7 |
| 3,364,190 A | 1/1968 | Emrick ....................... 260/93.7 |
| 3,645,992 A | 2/1972 | Elston ...................... 260/80.78 |
| 3,691,101 A | 9/1972 | Mertzweiller et al. ....... 252/455 |
| 4,068,136 A | 1/1978 | Minami ....................... 307/353 |
| 4,076,698 A | 2/1978 | Anderson et al. ......... 526/348.6 |
| 4,243,691 A | 1/1981 | Mohlenkamp, Jr et al. . 426/649 |
| 4,302,565 A | 11/1981 | Goeke et al. .................. 526/88 |
| 4,376,722 A | 3/1983 | Chester et al. .............. 252/430 |
| 4,440,871 A | 4/1984 | Lok et al. .................... 502/214 |
| 4,444,898 A | * 4/1984 | Schwartz et al. ............. 502/62 |
| 4,446,243 A | * 5/1984 | Chester et al. ................ 502/62 |
| 4,451,572 A | * 5/1984 | Cody .......................... 502/62 |
| 4,482,752 A | * 11/1984 | Mitchell et al. ............ 585/670 |
| 4,499,327 A | 2/1985 | Kaiser ........................ 585/640 |
| 4,532,225 A | * 7/1985 | Tsao et al. .................... 502/62 |
| 4,567,029 A | 1/1986 | Wilson et al. ............... 423/306 |
| 4,659,685 A | 4/1987 | Coleman, III et al. ...... 502/113 |
| 4,692,424 A | 9/1987 | Le Van Mao ................. 502/68 |
| 4,861,743 A | 8/1989 | Flank et al. ................. 502/214 |
| 5,070,052 A | 12/1991 | Brownscombe et al. ...... 502/60 |
| 5,096,684 A | 3/1992 | Guth et al. .................. 423/306 |
| 5,126,308 A | 6/1992 | Barger et al. ................ 502/214 |
| 5,302,362 A | 4/1994 | Bedard ....................... 423/306 |
| 5,382,696 A | * 1/1995 | Kiyoura et al. ............. 564/479 |
| 5,523,506 A | 6/1996 | Benazzi et al. ............. 585/481 |
| 5,625,104 A | 4/1997 | Beck et al. .................. 585/475 |
| 5,849,968 A | 12/1998 | Beck et al. .................. 585/481 |
| 5,892,079 A | 4/1999 | Wilson, Jr. ................... 556/11 |
| 5,912,393 A | 6/1999 | Barger et al. ................ 585/640 |
| 5,962,762 A | 10/1999 | Sun et al. .................... 585/640 |
| 5,981,417 A | 11/1999 | Drake .......................... 502/64 |
| 6,046,373 A | * 4/2000 | Sun ............................ 585/640 |
| 6,084,142 A | 7/2000 | Yao et al. .................... 585/407 |
| 6,107,534 A | 8/2000 | Drake et al. ................ 585/411 |
| 2002/0151758 A1 | * 10/2002 | Das et al. .................... 585/467 |

FOREIGN PATENT DOCUMENTS

| | | | |
|---|---|---|---|
| EP | 1 142 833 | 1/2001 | .......... C01B/36/06 |
| GB | 1108262 | 3/1968 | ............. C07C/5/18 |
| WO | WO 97/21652 | 6/1997 | .......... C07C/11/02 |
| WO | WO 97/26989 | 7/1997 | ............ B01J/29/04 |

OTHER PUBLICATIONS

Breck, Zeolite Molecular Sieves, p. 460–461, 1974.*
Paulino et al., "Ethylene Polymerization with Zirconocene–MAO supported on Molecular Sieves", *Studies in Surface Science and Catalysis*, vol. 130, pp. 929–934 (2000).
Yamamoto et al, "Organic Functionalization of Mesoporous Molecular Sieves with Grignard Reagents", *Microporous and Mesoporous Materials*, vol. 44, pp. 459–464 (2001).
K. Yamamoto et al., "Organic Functionalization of Mesoporous Molecular Sieves with Gringnard Reagents" *Microporous and Mesoporous Materials*, pp. 459–464 (2001).
H. Beyer et al., "Ristveld Refinement and EXAFS Studies of the Incorporation of Zn(II) and Mn(II) Cations into Tetrahedral Framework Sites of AIPO4–$^{34}$ Molecular Sieve" *Microporous and Mesoporous Materials*, vol. 94 pp 232–239 (1995).
Gonzalez et al., "Synthesis and Characerization of ZnAPO–3 Molecular Sieve with CHA Structure Type" *Microporous and Mesoporous Materials*, 25 pp. 103–108 (1998).
S. Dapurkar et al., "Nanosized Metal Oxides in the Mesopores of MCM–41 and MCM–48 Silicates", *Catalysts Today*, vol. 68, pp. 63–68 (2001).
L. Zhang et al., "Vapor–phase Transport Synthesis of ZnAPO–34 Molecular Sieve" Chemical Engineering, California Institute of Technology, Pasadene, CA 91125, pp. 210–241 (1998).
R. Grasselli et al., "Structure–Activity and Selectivity Relationships in Heterogeneous Catalysis" Elsevier Science Publishers B. V. Amsterdam pp. 233–242 (1991).
H. Chon et al., "Progress in Zeolite and Microporous Materials Studies in Surface Science and Catalysis" vol. 105 pp. 501–508 (1997).
Wendelblo et al., "Synthesis, Characterization and Catalytic Testing of SAPO–18, MgAPO–18, and ZnAPO–18 in the MTO reaction" Applied Catalysis A: General 142 pp. 1197–1207 (1996).

* cited by examiner

*Primary Examiner*—David R. Sample

(57) ABSTRACT

A method for the post synthesis modification of molecular sieves with organometallic reagents. The method may be used for large pore molecular sieves and small pore molecular sieves, such as SAPO-34. SAPO-34 is a useful catalyst for the conversion of oxygenates, such as methanol, to olefins. Post synthesis organometallic modification improves catalyst performance and increases light olefin selectivity in the conversion of methanol to olefins.

59 Claims, 4 Drawing Sheets

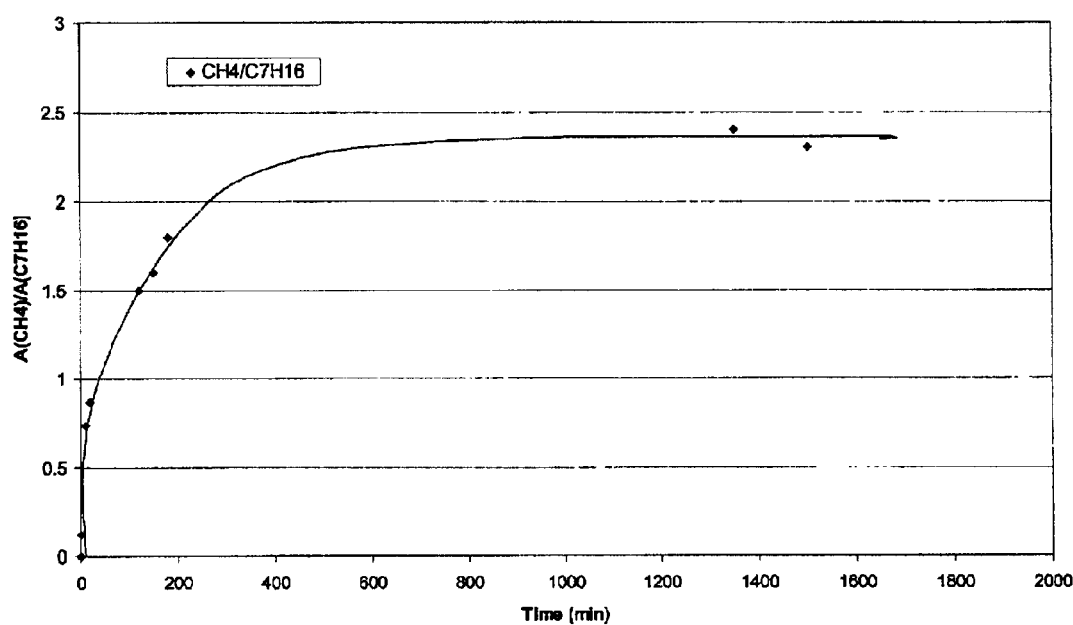
Figure 1. Evolution of methane during ZnMe$_2$ treatment of SAPO-34 in heptane (Example 17)

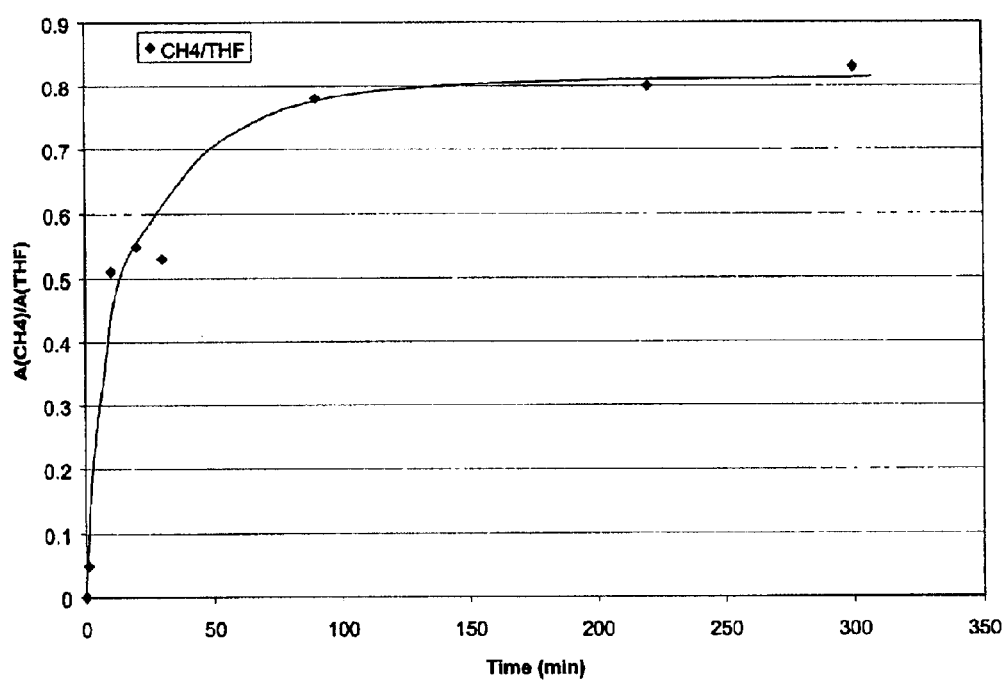
Figure 2. Evolution of methane during MeMgBr treatment of SAPO-34 in toluene/THF (Example 18)

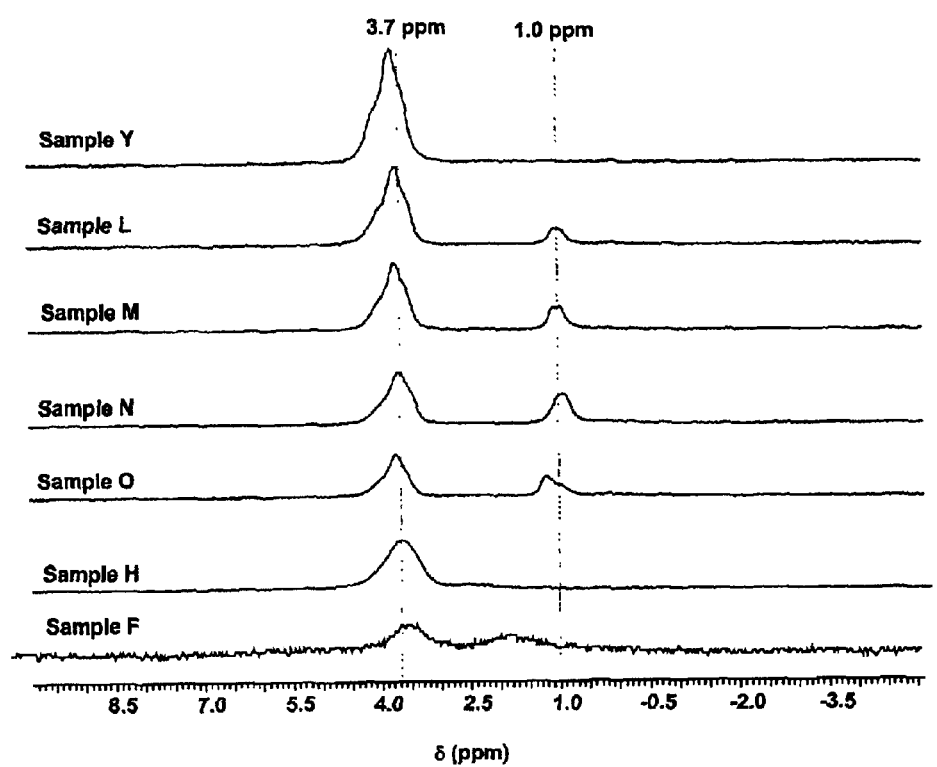
Figure 3. MAS $^1$H NMR of modified SAPO-34 via different methods

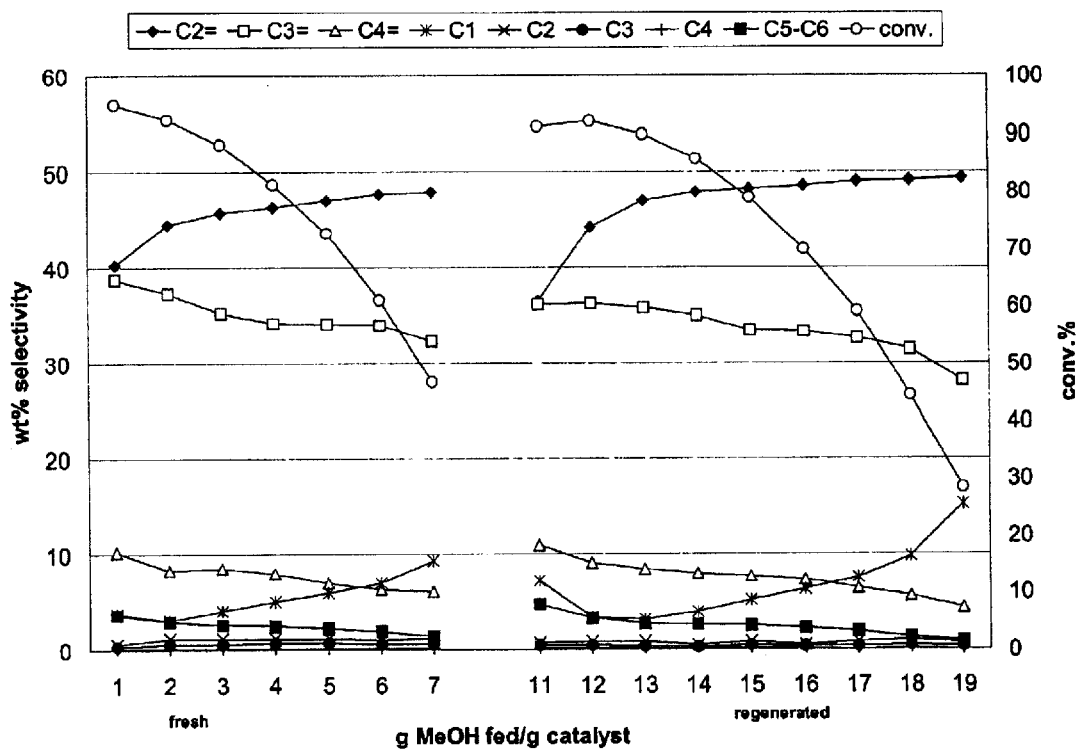
Figure 4. Conversion and selectivity for fresh (left) and regenerated (right) SAPO-34 modified with $ZnMe_2$ (Example 24, Sample B)

INTERIOR SURFACE MODIFICATIONS OF MOLECULAR SIEVES WITH ORGANOMETALLIC REAGENTS AND THE USE THEREOF FOR THE CONVERSION OF OXYGENATES TO OLEFINS

FIELD OF THE INVENTION

The invention is directed to a method for modifying the interior surface of molecular sieves, the modified molecular sieves, and a method for converting an oxygenate feedstock to a product, including an olefin. In particular, the invention is directed to modifying a silicoaluminophosphate molecular sieve with an organometallic reagent, the modified silicoaluminophosphate molecular sieve, and a method for converting an oxygenate feedstock to a product, including an olefin, with the modified silicoaluminophosphate molecular sieve.

BACKGROUND OF THE INVENTION

Olefins, particularly light olefins, have been traditionally produced from petroleum feedstocks by either catalytic or steam cracking. Oxygenates, however, are becoming an alternative feedstock for making light olefins, particularly ethylene and propylene. Promising oxygenate feedstocks are alcohols, such as methanol and ethanol, dimethyl ether, methyl ethyl ether, diethyl ether, dimethyl carbonate, and methyl formate. Many of these oxygenates can be produced from a variety of sources including synthesis gas derived from natural gas; petroleum liquids; and carbonaceous materials, including coal. Because of the relatively low-cost of these sources, alcohol, alcohol derivatives, and other oxygenates have promise as an economical, non-petroleum source for light olefin production.

One way of producing olefins is by the catalytic conversion of methanol using a silicoaluminophosphate (SAPO) molecular sieve catalyst. For example, U.S. Pat. No. 4,499,327 to Kaiser, discloses making olefins from methanol using a variety of SAPO molecular sieve catalysts. The process can be carried out at a temperature between 300° C. and 500° C., a pressure between 0.1 atmosphere to 100 atmospheres, and a weight hourly space velocity (WHSV) of between 0.1 and 40 $hr^{-1}$.

Inui (*J. Chemical Society Chem. Commun.* p.205, 1990) has shown that the selectivity to ethylene can be increased when methanol is contacted with a nickel-substituted SAPO-34 rather than an unsubstituted SAPO-34. In this case, nickel substitution occurred into the SAPO-34 framework.

In contrast to the work of Kaiser and Inui, metal incorporation may also take place post-synthesis, that is, following the synthesis of the molecular sieve framework. For example, U.S. Pat. No. 5,962,762 to Sun et al. teaches a process for converting methanol to light olefins using a metal-incorporated SAPO catalyst. An aqueous metal solution, preferably a nickel or cobalt containing solution, is adsorbed onto the SAPO molecular sieve by allowing the solution to remain in contact with the SAPO overnight at ambient conditions. The treated molecular sieve is then separated from the solution and dried. U.S. Pat. Nos. 5,625,104 and 5,849,968 to Beck at al. teach a process of incorporating alkali earth and alkaline earth metals into a zeolitic catalyst by pretreating the zeolite with an organosilicon or poly-oxo silicon compound followed by the treatment of a metal solution. U.S. Pat. No. 4,692,424 to Le Van Mao teaches a process for the dry incorporation of manganese ions on the external reactive sites of ZSM catalysts by adding a minimum amount of an aqueous manganese solution to form a malleable paste and extruding the paste under pressure.

Post-synthesis metal incorporation of zeolite catalysts is used for other processes as well. U.S. Pat. No. 6,084,142 to Yao et al. teaches treating a zeolite catalyst with a zinc component in an aqueous solution followed by steam treatment for the conversion of hydrocarbons to lower olefins. There is no teaching of conversion of methanol to olefins.

Yamamoto et al. (*Microporous and Mesoporous Materials* 44–45, Organic Functionalization of Mesoporous Molecular Sieves with Grignard Reagents, p.459–464, 2001) teach post-synthesis organic functionalization of MCM-41 in a two step procedure. MCM-41 is first modified by alcohols, which leads to the esterification of surface silanol groups (converting Si—OH to Si—OR) and then allowed to react with a Grignard reagent R'MgX which converts Si—OR to Si—R'. The two step procedure must be followed since Si—OH spoils Grignard reagent R'MgX to form Si—O—MgX and R'—H. There is no teaching of conversion of methanol to olefins.

PCT Application WO 97/26989 teaches adding a transition metal hydrogenation component in a non-aqueous solvent to a non-zeolitic molecular sieve after synthesis for hydrocracking and catalytic dewaxing. The hydrogenation component is in the form of a sulfide, halide, oxide, carboxylate, and the like. There is no teaching of conversion of methanol to olefins.

In spite of the prior efforts to modify molecular sieves, the need to modify the surface, in particular the interior surface, of small pore molecular sieves such as silicoaluminophosphates (SAPO) remains. Consequently, there is still a need to find an improved molecular sieve or molecular sieve catalyst that exhibits high ethylene and/or propylene selectivity in the conversion of methanol to light olefins.

BRIEF DESCRIPTION OF THE DRAWINGS

FIG. 1 shows the evolution of methane during dimethyl zinc treatment of SAPO-34 in heptane.

FIG. 2 shows the evolution of methane during methylmagnesium bromide treatment of SAPO-34 in a mixture of toluene and tetrahydrofuran (THF).

FIG. 3 shows MAS $^1$H NMR of zinc modified SAPO-34 via different zinc modification methods.

FIG. 4 shows conversion and selectivity data for fresh and regenerated SAPO-34 modified with dimethyl zinc.

SUMMARY OF THE INVENTION

The invention provides a method for making an organometallic treated molecular sieve comprising:

a) providing a molecular sieve having at least one hydroxyl group;

b) contacting said molecular sieve with a solution comprising an organometallic compound and a non-proton donating solvent, wherein said organometallic compound comprises at least one metal bound to at least one alkyl group; and c) separating the organometallic treated molecular sieve from the solution.

The invention relates to an organometallic treated molecular sieve, particularly a silicoaluminophosphate molecular sieve, obtainable by the method of the present invention. The organometallic compound is incorporated into, onto, or within the molecular sieve by chemical reactions to modify both the internal and external surfaces, preferably the internal surface, of the molecular sieve.

The invention further relates to a catalyst comprising an organometallic treated molecular sieve, particularly a silicoaluminophosphate molecular sieve, according to the invention.

The invention also relates to a method of making an olefinic product, wherein the catalyst comprising an organometallic treated molecular sieve, particularly a silicoaluminophosphate molecular sieve, is contacted with a feedstock comprising at least one organic compound that contains at least one oxygen atom (oxygenate) under conditions suitable to convert the oxygenate into olefins.

Organometallic reagents comprising at least one metal bound to at least one alkyl group, such as methyl lithium, butyl lithium, dimethyl zinc, diethyl zinc, ethylmagnesium bromide, methylmagnesium bromide, trimethyl gallium, thiethyl gallium, tetraethyl germanium, and tetramethyl germanium can be used in the method of the present invention.

The method of the present invention can be used for large pore molecular sieves, but are especially important for the modification of small pore molecular sieves such as SAPO-34. SAPO-34, an eight-ring silicoaluminophosphate catalyst, is a preferred catalyst for the conversion of oxygenates, especially methanol, to olefins.

We have discovered a post-synthesis modification method using organometallic compounds as the modifying reagents. With this modification, metal species are incorporated into, onto, or within the molecular sieves through chemical reactions with the hydroxyl groups in the molecular sieves. The proper size of the reagent and the nature of the chemical reactions determine the location, preferably on the interior surface of the molecular sieve, of the metal introduced. Compared to conventional post-synthesis methods, the method of the present invention requires mild conditions and offers control of reaction mechanisms such as the loading of the metal, the site and degree of reaction, and the location of the metal, therefore offering a controllable approach to improve catalyst performance.

Post-synthesis organometallic modification, according to the method of the present invention, provides a vehicle to improve catalyst performance for conversion of methanol to olefins by fine-tuning acidity and pore volume of the molecular sieve. As a result, both acidity and pore volume are modified as reflected in changes in catalyst structure and performance. For example, we have found that treating SAPO-34 with dimethyl zinc increases light olefin selectivity, with increasing ethylene to propylene ratio as zinc loading increases.

We have discovered a method to modify the interior surfaces of molecular sieves employing organometallic reagents in non-proton donating solvents. Increases in light olefin selectivity, especially ethylene selectivity, can be achieved, using the method of the present invention. For example, dimethyl zinc, $Zn(CH_3)_2$, can easily get into the cage of SAPO-34 and react at the interior acid sites, resulting in interior surface modification of the molecular sieve. The yield of ethylene from methanol to olefin (MTO) conversion with SAPO-34 can be increased when SAPO-34 is modified with dimethyl zinc.

DETAILED DESCRIPTION OF THE INVENTION

This invention relates to a method for modifying molecular sieves, particularly silicoaluminophosphate molecular sieves, with an organometallic compound. When these organometallic modified molecular sieves are used in the catalytic conversion of methanol to light olefins, they exhibit higher selectivities to ethylene and/or propylene than the corresponding unmodified molecular sieve.

According to the present invention, molecular sieves are treated with organometallic reagents after the molecular sieve structures are formed. Incorporating the metal after the molecular sieve has been prepared has several advantages over that of metal incorporation during molecular sieve synthesis. The physical characteristics of the molecular sieve, such as particle and pore size, can be varied prior to metal incorporation. As a result, post-synthesis techniques provide wider possibilities in molecular sieve preparation and screening. For example, a particular metal can be tested over a wide variety of molecular sieves, or a particular molecular sieve can be tested over a wide range of metals. Also, the molecular sieve structures obtained by the various methods can differ significantly, which is reflected in significant differences in catalytic behaviors.

Molecular sieves that may be used in accordance with the present invention are silicoaluminophosphates (SAPOs) and aluminosilicates having an average pore opening of at least 3 Angstroms. Suitable molecular sieves include, but are not limited to the structural types of AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, and THO and substituted examples of these structural types, as described in Ch. Baerlocher, W. M. Meier, and D. H. Olson, Atlas of Zeolite Framework Types, fifth edition (Elsevier, 2001), incorporated herein by reference. Structural types of medium pore molecular sieves useful in the present invention include, but are not limited to, MFI, MEL, MTW, EUO, MTT, HEU, FER, AFO, AEL, TON, and substituted examples of these structural types, as described in the Atlas of Zeolite Framework Types, previously incorporated herein by reference. Aluminosilicates that may be used in accordance with the present invention include, but are not limited to, ZSM-34, chabazite and erionite. SAPO molecular sieves that may be used in accordance with the invention include, but are not limited to, SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, and mixtures thereof. Preferred are SAPO-18, SAPO-34, SAPO-35, SAPO-44, SAPO-47 and SAPO-56, particularly SAPO-34, intergrowths of SAPO-34 and SAPO-18, and mixtures thereof. As used herein, the term mixture is synonymous with combination and is considered a composition of matter having two or more components in varying proportions, regardless of their physical state.

Silicoaluminophosphate molecular sieves (SAPOs) comprise a three-dimensional microporous crystal framework structure of $(SiO_2)$, $(AlO_2)$ and $(PO_2)$ corner sharing tetrahedral units. The way Si is incorporated into the structure can be determined by Si MAS NMR. (See Blackwell and Patton, J. Phys. Chem., 92, 3965 (1988)) The desired SAPO molecular sieves will exhibit one or more peaks in the $^{29}$Si MAS NMR, with a chemical shift $\delta(Si)$ in the range of −88 to −96 ppm and with a combined peak area in that range of at least 20% of the total peak area of all peaks with a chemical shift $\delta(Si)$ in the range of −88 ppm to −115 ppm, where the $\delta(Si)$ chemical shifts refer to external tetramethylsilane (TMS).

SAPO molecular sieves are generally classified as being microporous materials having 8, 10, or 12 membered ring structures. These ring structures can have an average pore size ranging from about 3–15 Angstroms. Preferred for MTO conversion are the small pore SAPO molecular sieves having an average pore opening of at most about 6 Angstroms, preferably an average pore opening of at most about 5.5 Angstroms, and more preferably at most about 4.2 Angstroms. The average pore opening is at least about 3 Angstroms, preferably at least about 3.5 Angstroms, and more preferably at least about 3.8 Angstroms. These pore openings are typical of molecular sieves having 8 membered rings.

SAPO molecular sieves comprise a molecular framework of corner-sharing $(SiO_2)$, $(AlO_2)$ and $(PO_2)$ tetrahedral units. Molecular sieves with this type of framework such as SAPO-34 are effective in converting feedstocks containing oxygenates into olefin products.

The $(PO_2)$ tetrahedral units within the framework structure of the molecular sieve of this invention can be provided by a variety of compositions. Examples of these phosphorus-containing compositions include phosphoric acid, organic phosphates such as triethyl phosphate, and aluminophosphates. The phosphorous-containing compositions are mixed with reactive silicon and aluminum-containing compositions under the appropriate conditions to form the molecular sieve.

The $(AlO_2)$ tetrahedral units within the framework structure can be provided by a variety of compositions. Examples of these aluminum-containing compositions include aluminum alkoxides such as aluminum isopropoxide, aluminum phosphates, aluminum hydroxide, sodium aluminate, and pseudoboehmite. The aluminum-containing compositions are mixed with reactive silicon and phosphorus-containing compositions under the appropriate conditions to form the molecular sieve.

The $(SiO_2)$ tetrahedral units within the framework structure can be provided by a variety of compositions. Examples of these silicon-containing compositions include silica sols and silicon alkoxides such as tetraethyl orthosilicate.

In order to prepare a silicoaluminophosphate molecular sieve, the silicon-containing compositions are mixed with reactive aluminum and phosphorus-containing compositions under the appropriate conditions to form the molecular sieve.

The silicoaluminophosphates may also contain one or more templates. Templates are structure directing or affecting agents, and typically contain nitrogen, phosphorus, oxygen, carbon, hydrogen or a combination thereof, and can also contain at least one alkyl or aryl group, with 1 to 8 carbons being present in the alkyl or aryl group. Mixtures of two or more templates can produce mixtures of different sieves or predominantly one sieve where one template is more strongly structure-directing than another.

Representative templates include tetraethyl ammonium salts, cyclopentylamine, aminomethyl cyclohexane, piperidine, diethylamine, triethylamine, cyclohexylamine, tri-ethyl hydroxyethylamine, morpholine, dipropylamine (DPA), pyridine, isopropylamine and combinations thereof. Preferred templates are diethylamine, triethylamine, cyclohexylamine, piperidine, pyridine, isopropylamine, tetraethyl ammonium salts, dipropylamine, and mixtures thereof. The tetraethyl ammonium salts include tetraethyl ammonium hydroxide (TEAOH), tetraethyl ammonium phosphate, tetraethyl ammonium fluoride, tetraethyl ammonium bromide, tetraethyl ammonium chloride, tetraethyl ammonium acetate. Preferred tetraethyl ammonium salts are tetraethyl ammonium hydroxide and tetraethyl ammonium phosphate. Particularly preferred templates are triethylamine (TEA) and tetraethyl ammonium hydroxide (TEAOH).

The SAPO molecular sieves are synthesized by hydrothermal crystallization methods generally known in the art. See, for example, U.S. Pat. Nos. 4,440,871; 4,861,743; 5,096,684; and 5,126,308, the methods of making of which are fully incorporated herein by reference. A reaction mixture is formed by mixing together reactive silicon, aluminum and phosphorus components, along with at least one template. Generally the mixture is sealed and heated, preferably under autogenous pressure, to a temperature of at least 100° C., preferably from 100–250° C., until a crystalline product is formed. Formation of the crystalline product can take anywhere from around 2 hours to as much as 2 weeks. In some cases, stirring, tumbling or seeding with crystalline material will facilitate the formation of the product.

Typically, the molecular sieve product is formed in solution. It can be recovered by standard means, such as by centrifugation or filtration. The product can also be washed, recovered by the same means, and dried. As a result of the crystallization process, the recovered sieve contains within its pores at least a portion of the template used in making the initial reaction mixture.

According to the method of the present invention, the molecular sieve may be calcined prior to contacting with the organometallic compound. The molecular sieve may be calcined to remove at least about 90%, preferably at least about 95%, and more preferably at least about 99% of the template. Typically, the molecular sieve is calcined at a temperature of at least about 300° C., preferably at least about 450° C., more preferably at least about 550° C. and at a temperature of at most about 800° C., preferably at most about 750° C., and more preferably at most about 700° C. The molecular sieve is calcined for a period of time of at least about 1 hour, preferably at least about 2 hours, more preferably at least about 3 hours and for a period of time of at most about 24 hours, preferably at most about 12 hours, and more preferably at most about 10 hours.

The calcined molecular sieves are then treated with a solution containing an organometallic compound and a non-proton donating solvent. No acid treatment or steam treatment of the molecular sieve is required by the method of the present invention.

The organometallic compound is defined as a compound having at least one metal bound to at least one alkyl group. The alkyl group is linear and may have up to at most about twenty (20) carbon atoms, preferably at most about twelve (12) carbon atoms, and more preferably at most about six (6) carbon atoms.

Metals useful according to the present invention are selected from the group consisting of Group 1 to Group 14, and mixtures thereof. See *The Chemistry of the Elements*, Second Edition, 1998. Suitable metals include, but are not limited to, lithium, gallium, germanium, magnesium, zinc, and mixtures thereof.

Suitable organometallic compounds include, but are not limited to, methyl lithium, butyl lithium, dimethyl zinc, diethyl zinc, ethylmagnesium bromide, methylmagnesium bromide, trimethyl gallium, triethyl gallium, tetraethyl germanium, and tetramethyl germanium and mixtures thereof. Dimethyl zinc is the preferred organometallic compound.

The concentration of organometallic compound in the solution is typically at least about 0.001 M, preferably at least about 0.005 M, and more preferably at least about 0.01 M. The concentration of organometallic compound in the solution is typically at most about 10.0 M, preferably at most about 5.0 M, and more preferably at most about 3.0 M.

Suitable non-proton donating solvents (anhydrous grade) include, but are not limited to, linear or branched alkanes or alkenes having a carbon number between five (5) and twenty (20), such as heptane; halogen-substituted alkanes having more than one (1) carbon, where the halogen can be fluorine or chlorine; ethers; ketones; sulfoxides; heterocyclic compounds, such as tetrahydrofuran, substituted pyridine or unsubstituted pyridine; aromatic compounds, such as benzene, toluene, or xylenes; and mixtures thereof.

The organometallic compound containing solution is contacted the molecular sieve, with or without stirring, under autogenous pressure in a reaction vessel. The reaction mixture may or may not be heated and is typically at a temperature of at least about −40° C., preferably at least about −25° C., more preferably at least about 0° C. and at a temperature of at most about 200° C., preferably at most about 150° C., and more preferably at most about 100° C.

The organometallic compound is contacted with the molecular sieve for a sufficient period of time depending upon the process temperature, the pressure, the type of organometallic compound solution used, the concentration of the organometallic compound in solution, and the type of molecular sieve used. Generally, the reaction is allowed to take place for several hours. The reaction takes place for a time of at least about 1 hour, preferably at least about 2 hours, more preferably at least about 3 hours and for a time of at most 48 hours, preferably at most about 24 hours, and more preferably at most about 20 hours. It is to be understood that one of ordinary skill in the art will know how to vary the time of contacting depending upon each of these parameters.

At this stage, one obtains what may be called an organometallic treated molecular sieve which is then separated from the non-proton donating solvent. The separated molecular sieve is then washed with one or more organic solvents to remove traces of unreacted or loosely bound organometallic compound. Suitable organic solvents include, but not limited to, methanol, ethanol, 2-propanol, diethyl ether, acetone, hexane, heptane, tetrahydrofuran, and toluene. The washed molecular sieve is dried, for example at 110° C. overnight.

The amount of metal disposed into, onto, or within the pores of the organometallic modified molecular sieve is such that the molecular sieve comprises at least about 0.05 percent by weight metal, preferably at least about 0.5 percent by weight metal, more preferably at least about 1.0 percent by weight metal and at most about 20 percent by weight metal, preferably at most about 10 percent by weight metal, and more preferably at most about 8 percent by weight metal.

The organometallic treated molecular sieve can be further contacted with a solution of the same or different organometallic compound according to the method of the present invention. Multiple cycles of contacting the organometallic solution with the molecular sieve can be carried out, if required, to achieve the desired degree of metal loading.

After the organometallic treatment, the resultant metal species is disposed into, onto, or within the molecular sieves. The metal species is introduced through chemical reactions with the hydroxyl groups of the molecular sieve, wherein the metal species is disposed within the pores, on the internal surfaces of the molecular sieve, and/or on the external surfaces of the molecular sieve. Under the conditions used according to the method of the present invention, the alkyl group of the organometallic compound reacts with the hydroxyl groups forming an alkane, such as methane or ethane, and the metal species is attached to the sites of the reactive hydroxyl groups, either within the pores, at the internal and/or external surfaces of the molecular sieve.

After the organometallic treated molecular sieve is washed and dried, the molecular sieve may be calcined or partially calcined. Typically, the molecular sieve of the invention is calcined, with or without oxygen, prior to use, for example, in a conversion reactor. The organometallic treated molecular sieve is calcined at a temperature of at least about 300° C., preferably at least about 450° C., more preferably at least about 550° C. and at a temperature of at most about 800° C., preferably at most about 750° C., and more preferably at most about 700° C.

The molecular sieve is calcined for a period of time of at least about 1 hour, preferably at least about 2 hours, more preferably at least about 3 hours and for a period of time of at most about 24 hours, preferably at most about 12 hours and more preferably at most about 10 hours. One thus obtains a calcined organometallic treated molecular sieve.

The organometallic treated molecular sieves of the present invention are useful as catalysts in the conversion of feedstocks containing at least one organic compound which contains at least one oxygen atom (hereinafter referred to as an oxygenate) into light olefins. For this purpose, the silicoaluminophosphates may be used in combination or in admixture with other components.

Another embodiment of this invention is the composition of the organometallic modified molecular sieves, particularly organometallic modified SAPO-34. For example, when dimethyl zinc is used to modify SAPO-34, a new zinc-containing molecular sieve is obtained. This new material has a signature peak that appears around $\delta=1.0$ ppm in the MAS $^1$H NMR.

The microporosity of the organometallic modified molecular sieve can be measured by its methanol uptake capacity. The organometallic modified molecular sieves have reduced methanol uptake capacity as compared to unmodified molecular sieves, reflecting decreased pore volume. The decreased pore volume is a result of interior surface modification by the organometallic reagents.

An aluminophosphate (ALPO) molecular sieve may be used alone or in combination with the silicoaluminophosphate molecular sieves of the present invention. Aluminophosphate molecular sieves are crystalline microporous oxides which can have an $AlPO_4$ framework. They can have additional elements within the framework, typically have uniform pore dimensions ranging from about 3 angstroms to about 10 angstroms, and are capable of making size selective separations of molecular species. More than two dozen structure types have been reported, including zeolite topological analogues. A more detailed description of the background and synthesis of aluminophosphates is found in U.S. Pat. No. 4,310,440, which is incorporated herein by reference in its entirety. Preferred ALPOs are ALPO-5, ALPO-11, ALPO-18, ALPO-31, ALPO-34, ALPO-36, ALPO-37, and ALPO-46.

The ALPOs can also include a metal substituent in its framework. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions. Members of this class and their preparation are described in U.S. Pat. No. 4,567,029, incorporated herein by reference in its entirety.

The metal containing ALPOs have a three-dimensional microporous crystal framework structure of $MO_2$, $AlO_2$ and PO$_2$ tetrahedral units. These as manufactured structures (which contain template prior to calcination) can be represented by empirical chemical composition, on an anhydrous basis, as:

mR: $(M_xAl_yP_z)O_2$ wherein R represents at least one organic templating agent present in the intracrystalline pore system; m represents the moles of R present per mole of $(M_xAl_yP_z)O_2$ and has a value of from zero to 0.3, the maximum value in each case depending upon the molecular dimensions of the templating agent and the available void volume of the pore system of the particular metal aluminophosphate involved, x, y, and z represent the mole fractions of the metal M, (i.e. magnesium, manganese, zinc and cobalt), aluminum and phosphorus, respectively, present as tetrahedral oxides The metal containing ALPOs are sometimes referred to by the acronym as MeAPO. Also in those cases where the metal Me in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

The organometallic treated SAPO molecular sieves of the present invention can also be admixed (i.e. blended, formulated) with other materials. Once prepared, the resulting composition is typically referred to as a SAPO catalyst, with the catalyst comprising the SAPO molecular sieve. Materials which can be blended with the molecular sieve can be various inert or catalytically active materials, or various binder materials. These materials include compositions such as kaolin and other clays, various forms of rare earth metals, metal oxides, other non-zeolite catalyst components, zeolite catalyst components, alumina or alumina sol, aluminum chlorhydrol, titania, zirconia, magnesia, thoria, beryllia, quartz, silica or silica or silica sol, and mixtures thereof. Preferably an alumina binder such as aluminum chlorhydrol, and/or one or more clays, such as kaolin, is used in combination with the molecular sieve of the invention. These components are also effective in reducing, inter alia, overall catalyst cost, acting as a thermal sink to assist in heat shielding the catalyst during regeneration, densifying the catalyst and increasing catalyst strength.

Preferably an alumina binder such as aluminum chlorhydrol, and/or one or more clays, such as kaolin, is used in combination with the molecular sieve of the invention. If the molecular sieve is in the dry from, a fluid, such as water, is added to form a slurry. More often, however, the catalyst is prepared following the preparation of the molecular sieve which is maintained as a slurry from the preceding crystallization step. The other components are then added to the slurried molecular sieve as either dry solids and/or as slurries. This final slurry having a specific solid content and particle size is mixed until a relatively uniform distribution of all components is obtained. The uniformly mixed slurry is then spray dried or extruded to form the catalyst.

Additional molecular sieve materials can be included as a part of the SAPO catalyst composition or they can be used as separate molecular sieve catalysts alone or in admixture with the SAPO catalyst if desired. Structural types of small pore molecular sieves that are suitable for use in this invention include AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof. Structural types of medium pore molecular sieves that are suitable for use in this invention include LEV, MFI, MEL, MTW, EUO, MTT, HEU, FER, AFO, AEL, TON, and substituted forms thereof. These small and medium pore molecular sieves are described in greater detail in the Atlas of Zeolite Framework Types, which is previously incorporated herein by reference. Preferred molecular sieves which can be used alone or combined with a silicoaluminophosphate catalyst include ZSM-5, ZSM-34, erionite, levyne and chabazite.

After formulation, the catalyst composition of the invention typically comprises at least about 1%, preferably at least about 5%, and more preferably at least about 10%, by weight of molecular sieve. The catalyst composition typically comprises at most about 99%, preferably at most about 90%, and more preferably at most about 80%, by weight of molecular sieve. The catalyst particles generally have a size of at least about 20 $\mu$, preferably at least about 30 $\mu$, and more preferably at least about 50 $\mu$. The catalyst particles generally have a size of at most about 3,000$\mu$, preferably at most about 200 $\mu$, and more preferably at most about 150$\mu$.

The catalyst particles can be subjected to a variety of treatments to achieve the desired physical and chemical characteristics. Such treatments include, but are not necessarily limited to hydrothermal treatment, calcination, acid treatment, base treatment, milling, ball milling, grinding, spray drying, and combinations thereof.

The catalyst particles containing an organometallic treated molecular sieve according to the present invention are useful as catalysts for the conversion of hydrocarbons, in particular for the catalytic conversion of feedstocks containing at least one organic compound containing at least one oxygen atom (oxygenate) to light olefins. Accordingly, a third aspect of the invention relates to a method of making an olefin product, wherein the catalyst of the invention is contacted with a feedstock comprising at least one oxygenate under conditions suitable to convert the oxygenate into olefins.

In this aspect of the invention, a feedstock containing at least one oxygenate, and optionally a diluent or a hydrocarbon added separately or mixed with the oxygenate, is contacted with a catalyst containing a SAPO molecular sieve in a reaction zone or volume. The volume in which such contact takes place is herein termed the reactor, which may be a part of a reactor apparatus or reaction system. Another part of the reaction system may be a regenerator, which comprises a volume wherein carbonaceous deposits (or coke) on the catalyst resulting from the olefin conversion reaction are removed by contacting the catalyst with regeneration medium.

The oxygenate feedstock of this invention comprises at least one organic compound which contains at least one oxygen atom (oxygenate), such as aliphatic alcohols, ethers, carbonyl compounds (aldehydes, ketones, carboxylic acids, carbonates, esters and the like). When the oxygenate is an alcohol, the alcohol can include an aliphatic moiety having from 1 to 10 carbon atoms, more preferably from 1 to 4 carbon atoms. Representative alcohols include but are not necessarily limited to lower straight and branched chain aliphatic alcohols and their unsaturated counterparts. Examples of suitable oxygenate compounds include, but are not limited to: methanol; ethanol; n-propanol; isopropanol; C$_4$–C$_{20}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, dimethyl ether, or a mixture thereof.

The method of making the preferred olefin product in this invention can include the additional step of making these compositions from hydrocarbons such as oil, coal, tar sand, shale, biomass and natural gas. Methods for making the compositions are known in the art. These methods include fermentation to alcohol or ether, making synthesis gas, then converting the synthesis gas to alcohol or ether. Synthesis gas can be produced by known processes such as steam reforming, autothermal reforming and partial oxidization.

One or more inert diluents may be present in the feedstock, for example, in an amount of from 1 to 99 molar percent, based on the total number of moles of all feed and diluent components fed to the reaction zone (or catalyst). As defined herein, diluents are compositions which are essentially non-reactive across a molecular sieve catalyst, and primarily function to make the oxygenates in the feedstock less concentrated. Typical diluents include, but are not necessarily limited to helium, argon, nitrogen, carbon monoxide, carbon dioxide, water, essentially non-reactive paraffins (especially the alkanes such as methane, ethane, and propane), essentially non-reactive alkylenes, essentially non-reactive aromatic compounds, and mixtures thereof. The preferred diluents are water and nitrogen. Water can be injected in either liquid or vapor form.

Hydrocarbons can also be included as part of the feedstock, i.e., as co-feed. As defined herein, hydrocarbons included with the feedstock are hydrocarbon compositions which are converted to another chemical arrangement when contacted with molecular sieve catalyst. These hydrocarbons can include olefins, reactive paraffins, reactive alkylaromatics, reactive aromatics or mixtures thereof. Preferred hydrocarbon co-feeds include, propylene, butylene, pentylene, $C_4^+$ hydrocarbon mixtures, $C_5^+$ hydrocarbon mixtures, and mixtures thereof. More preferred as co-feeds are a $C_4^+$ hydrocarbon mixtures, with the most preferred being $C_4^+$ hydrocarbon mixtures which are obtained from separation and recycle of reactor product.

In the process of this invention, coked catalyst can be regenerated by contacting the coked catalyst with a regeneration medium to remove all or part of the coke deposits. This regeneration can occur periodically within the reactor by ceasing the flow of feed to the reactor, introducing a regeneration medium, ceasing flow of the regeneration medium, and then reintroducing the feed to the fully or partially regenerated catalyst. Regeneration may also occur periodically or continuously outside the reactor by removing a portion of the deactivated catalyst to a separate regenerator, regenerating the coked catalyst in the regenerator, and subsequently reintroducing the regenerated catalyst to the reactor. Regeneration can occur at times and conditions appropriate to maintain a desired level of coke on the entire catalyst within the reactor.

Catalyst that has been contacted with feed in a reactor is defined herein as feedstock exposed. Feedstock exposed catalyst will provide olefin conversion reaction products having substantially lower propane and coke content than a catalyst which is fresh and regenerated. A catalyst will typically provide lower amounts of propane as it is exposed to more feed, either through increasing time at a given feed rate or increasing feed rate over a given time.

At any given instant in time, some of the catalyst in the reactor will be fresh, some regenerated, and some coked or partially coked as a result of having not yet been regenerated. Therefore, various portions of the catalyst in the reactor will have been feedstock exposed for different periods of time. Since the rate at which feed flows to the reactor can vary, the amount of feed to which various portions of the catalyst can also vary. To account for this variation, the average catalyst feedstock exposure index (ACFE index) is used to quantitatively define the extent to which the entire catalyst in the reactor has been feedstock exposed.

As used herein, ACFE index is the total weight of feed divided by the total weight of molecular sieve (i.e., excluding binder, inerts, etc., of the catalyst composition) sent to the reactor. The measurement should be made over an equivalent time interval, and the time interval should be long enough to smooth out fluctuations in catalyst or feedstock rates according to the reactor and regeneration process step selected to allow the system to be viewed as essentially continuous. In the case of reactor systems with periodic regenerations, this can range from hours up to days or longer. In the case of reactor systems with substantially constant regeneration, minutes or hours may be sufficient.

Flow rate of catalyst can be measured in a variety of ways. In the design of the equipment used to carry the catalyst between the reactor and regenerator, the catalyst flow rate can be determined given the coke production rate in the reactor, the average coke level on catalyst leaving the reactor, and the average coke level on catalyst leaving the regenerator. In an operating unit with continuous catalyst flow, a variety of measurement techniques can be used. Many such techniques are described, for example, by Michel Louge, "Experimental Techniques", *Circulating Fluidized Beds*, Grace, Avidan, & Knowlton, eds., Blackie, 1997 (336–337), the descriptions of which are expressly incorporated herein by reference.

In this invention, only the molecular sieve in the catalyst sent to the reactor may be used in the determination of ACFE index. The catalyst sent to the reactor, however, can be either fresh or regenerated or a combination of both. Molecular sieve which may be recirculated to and from the reactor within the reactor apparatus (i.e., via ducts, pipes or annular regions), and which has not been regenerated or does not contain fresh catalyst, is not to be used in the determination of ACFE index.

In a preferred embodiment of this invention, a feed containing an oxygenate, and optionally a hydrocarbon, either separately or mixed with the oxygenate, is contacted with a catalyst containing a SAPO molecular sieve at process conditions effective to produce olefins in a reactor.

Any standard reactor system can be used, including fixed bed, fluid bed or moving bed systems. Preferred reactors are co-current riser reactors and short contact time, countercurrent free-fall reactors. Desirably, the reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to 1000 $hr^{-1}$, more preferably in the range of from about 20 $hr^{-1}$ to 1000 $hr^{-1}$, and most preferably in the range of from about 20 $hr^{-1}$ to 500 $hr^{-1}$. WHSV is defined herein as the weight of oxygenate, and hydrocarbon which may optionally be in the feed, per hour per weight of the molecular sieve content of the catalyst. Because the catalyst or the feedstock may contain other materials which act as inerts or diluents, the WHSV is calculated on the weight basis of the oxygenate feed, and any hydrocarbon which may be present, and the molecular sieve contained in the catalyst.

Preferably, the oxygenate feed is contacted with the catalyst when the oxygenate is in a vapor phase. Alternately, the process may be carried out in a liquid or a mixed vapor/liquid phase. When the process is carried out in a liquid phase or a mixed vapor/liquid phase, different conversions and selectivities of feed-to-product may result depending upon the catalyst and reaction conditions.

The process can generally be carried out at a wide range of temperatures. An effective operating temperature is at least about 200° C., preferably at least about 300° C., more preferably at least about 350° C. and a temperature of at most about 700° C., preferably at most about 650° C., and more preferably at most about 600° C. At the lower end of the temperature range, the formation of the desired olefin products may become markedly slow. At the upper end of the temperature range, the process may not form an optimum amount of product.

It is highly desirable to operate at a temperature of at least 300° C. and a Temperature Corrected Normalized Methane Sensitivity (TCNMS) of less than about 0.016. It is particularly preferred that the reaction conditions for making olefin from oxygenate comprise a WHSV of at least about 20 $hr^{-1}$ producing olefins and a TCNMS of less than about 0.016.

As used herein, TCNMS is defined as the Normalized Methane Selectivity (NMS) when the temperature is less than 400° C. The NMS is defined as the methane product yield divided by the ethylene product yield wherein each yield is measured on, or is converted to, a weight % basis. When the temperature is 400° C. or greater, the TCNMS is defined by the following equation, in which T is the average temperature within the reactor in ° C.:

$$TCNMS = \frac{NMS}{1 + (((T-400)/400) \times 14.84)}$$

The pressure also may vary over a wide range, including autogenous pressures. Effective pressures may be in, but are not necessarily limited to, oxygenate partial pressures at least 1 psia (6.9 kPa), preferably at least 5 psia (34.5 kPa). The process is particularly effective at higher oxygenate partial pressures, such as an oxygenate partial pressure of greater than 20 psia (137.9 kPa). Preferably, the oxygenate partial pressure is at least about 25 psia (172.4 kPa), more preferably at least about 30 psia (206.8 kPa). For practical design purposes it is desirable to operate at a methanol partial pressure of not greater than about 500 psia (3447.4 kPa), preferably not greater than about 400 psia (2757.9 kPa), most preferably not greater than about 300 psia (2068.4 kPa).

The conversion of oxygenates to produce light olefins may be carried out in a variety of catalytic reactors. Reactor types include fixed bed reactors, fluid bed reactors, and concurrent riser reactors as described in "Free Fall Reactor", *Fluidization Engineering*, D. Kunii and O. Levenspiel, Robert E. Krieger Publishing Co. NY, 1977, expressly incorporated herein by reference. Additionally, countercurrent free fall reactors may be used in the conversion process as described in U.S. Pat. No. 4,068,136 and "Riser Reactor", *Fluidization and Fluid-Particle Systems*, pages 48–59, F. A. Zenz and D. F. Othmo, Reinhold Publishing Corp., NY 1960, the detailed descriptions of which are also expressly incorporated herein by reference.

In a preferred embodiment of the continuous operation, only a portion of the catalyst is removed from the reactor and sent to the regenerator to remove the accumulated coke deposits that result during the catalytic reaction. In the regenerator, the catalyst is contacted with a regeneration medium containing oxygen or other oxidants. Examples of other oxidants include $O_3$, $SO_3$, $N_2O$, $NO$, $NO_2$, $N_2O_5$, and mixtures thereof. It is preferred to supply $O_2$ in the form of air. The air can be diluted with nitrogen, $CO_2$, or flue gas, and steam may be added. Desirably, the $O_2$ concentration in the regenerator is reduced to a controlled level to minimize overheating or the creation of hot spots in the spent or deactivated catalyst. The deactivated catalyst also may be regenerated reductively with $H_2$, CO, mixtures thereof, or other suitable reducing agents. A combination of oxidative regeneration and reductive regeneration can also be employed.

In essence, the coke deposits are removed from the catalyst during the regeneration process, forming a regenerated catalyst. The regenerated catalyst is then returned to the reactor for further contact with feed. Typical regeneration temperatures are in the range of 250–700° C., desirably in the range of 350–700° C. Preferably, regeneration is carried out at a temperature range of 450–700° C.

In one embodiment, the reactor and regenerator are configured such that the feed contacts the regenerated catalyst before it is returned to the reactor. In an alternative embodiment, the reactor and regenerator are configured such that the feed contacts the regenerated catalyst after it is returned to the reactor. In yet another embodiment, the feed stream can be split such that feed contacts regenerated catalyst before it is returned to the reactor and after it has been returned to the reactor. It is preferred that the catalyst within the reactor have an average level of coke effective for selectivity to ethylene and/or propylene. Preferably, the average coke level on the catalyst will be from about 2 wt. % to about 30 wt. %, more preferably from about 2 wt. % to about 20 wt. %. In order to maintain this average level of coke on catalyst, the entire volume of catalyst can be partially regenerated under conditions effective to maintain the desired coke content on catalyst. It is preferred, however, to recycle only a portion of the coked catalyst for feed contact without regenerating. This recycle can be performed either internal or external to the reactor. The portion of coked catalyst to be regenerated is preferably regenerated under conditions effective to obtain a regenerated catalyst having a coke content of less than 2 wt. %, preferably less than 1.5 wt. %, and most preferably less than 1.0 wt. %.

In order to make up for any catalyst loss during the regeneration or reaction process, fresh catalyst can be added. Preferably, the fresh catalyst is added to the regenerated catalyst after it is removed from the regenerator, and then both are added to the reactor. However, the fresh catalyst can be added to the reactor independently of the regenerated catalyst. Any amount of fresh catalyst can be added, but it is preferred that an ACFE index of at least 1.5 be maintained.

One skilled in the art will also appreciate that the olefins produced by the oxygenate-to-olefin conversion reaction of the present invention can be polymerized to form polyolefins, particularly polyethylene and polypropylene. Processes for forming polyolefins from olefins are known in the art. Catalytic processes are preferred. Particularly preferred are metallocene, Ziegler/Natta and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the olefin product with a polyolefin-forming catalyst at a pressure and temperature effective to form the polyolefin product.

A preferred polyolefin-forming catalyst is a metallocene catalyst. The preferred temperature range of operation is between 50 and 240° C. and the reaction can be carried out at low, medium or high pressure, being anywhere within the range of about 1 to 200 bars. For processes carried out in solution, an inert diluent can be used, and the preferred operating pressure range is between 10 and 150 bars, with a preferred temperature range of between 120 and 230° C. For gas phase processes, it is preferred that the temperature generally be within a range of 60 to 160° C., and that the operating pressure be between 5 and 50 bars.

In addition to polyolefins, numerous other olefin derivatives may be formed from the olefins recovered therefrom. These include, but are not limited to, aldehydes, alcohols, acetic acid, linear alpha olefins, vinyl acetate, ethylene dichloride and vinyl chloride, ethylbenzene, ethylene oxide, cumene, isopropyl alcohol, acrolein, allyl chloride, propylene oxide, acrylic acid, ethylene-propylene rubbers, and acrylonitrile, and trimers and dimers of ethylene, propylene or butylenes. The methods of manufacturing these derivatives are well known in the art, and therefore, are not discussed herein.

This invention will be better understood with reference to the following examples, which are intended to illustrate specific embodiments within the overall scope of the invention as claimed.

EXAMPLE 1

Calcination of SAPO-34 to Remove Template(s)

SAPO-34, is made by hydrothermal crystallization of a mixture containing water, a silica source, an alumina source, a phosphorus source, as well as tetraethylammonium hydroxide (TEAOH) and dipropyl amine (DPA) as the templating agents, and is hereinafter referred to as Sample X (uncalcined). Sample X is then calcined in air at 600° C. for 3 hours to remove the template(s) and stored at 200° C. before use. The solid obtained after calcination is hereinafter referred to as Sample Y.

EXAMPLE 2

Dimethyl Zinc Treatment for SAPO-34

Under an $N_2$ atmosphere, 1.6 g of SAPO-34 (Sample Y) is suspended in 50 ml of anhydrous heptane in a 100-ml round-bottom flask. Dimethyl zinc, 0.90 ml of 1.0 M solution in heptane, is slowly added to the mixture via a gas-tight syringe. The starting ratio of zinc to silicon in the SAPO-34 is 0.50. The mixture is stirred at room temperature for 20 hr and centrifuged. The isolated solid is then stirred in 50 ml of anhydrous methanol for 4 hr at room temperature, centrifuged, and dried at 105° C. for one day. The solid is calcined at 600° C. for 3 hr before use and hereinafter referred to as Sample A.

EXAMPLE 3

Dimethyl Zinc Treatment for SAPO-34

Under an $N_2$ atmosphere, 2.8 g of SAPO-34 (Sample Y), is suspended in 50 ml of anhydrous heptane in a 100-ml round-bottom flask. Dimethyl zinc, 0.84 ml of 1.0 M solution in heptane, is slowly added to the mixture via a gas-tight syringe. The starting ratio of zinc to silicon in the SAPO-34 is 0.25. The mixture is stirred at room temperature for 20 hr and centrifuged. The isolated solid is then stirred in 50 ml of anhydrous methanol for 4 hr at room temperature, centrifuged, and dried at 105° C. for one day. The solid is calined at 600° C. for 3 hr before use and hereinafter referred to as Sample B.

EXAMPLE 4

Dimethyl Zinc Treatment for SAPO-34

Under an $N_2$ atmosphere, 2.2 g of SAPO-34 (Sample Y) is suspended in 50 ml of anhydrous heptane in a 100-ml round-bottom flask. Dimethyl zinc, 1.40 ml of 1.0 M solution in heptane, is slowly added to the mixture via a gas-tight syringe. The starting ratio of zinc to silicon in the SAPO-34 is 0.60. The mixture is stirred at room temperature for 20 hr and centrifuged. The isolated solid is then stirred in 50 ml of anhydrous methanol for 4 hr at room temperature, centrifuged, and dried at 105° C. for one day. The solid is calcined at 600° C. for 3 hr before use and hereinafter referred to as Sample C.

EXAMPLE 5

Dimethyl Zinc Treatment for SAPO-34

Under an $N_2$ atmosphere, 1.6 g of SAPO-34 (Sample Y) is suspended in 50 ml of anhydrous heptane in a 100-ml round-bottom flask. Dimethyl zinc, 3.50 ml of 1.0 M solution in heptane, is slowly added to the mixture via a gas-tight syringe. The starting ratio of zinc to silicon in the SAPO-34 is 2.00. The mixture is stirred at room temperature for 20 hr and centrifuged. The isolated solid is then stirred in 50 ml of anhydrous methanol for 4 hr at room temperature, centrifuged, and dried at 105° C. for one day. The solid is calcined at 600° C. for 3 hr before use and hereinafter referred to as Sample D.

EXAMPLE 6

Dimethyl Zinc Treatment for SAPO-34

Under an $N_2$ atmosphere, 4.2 g of SAPO-34 (Sample Y) is suspended in 150 ml of anhydrous heptane in a 500-ml round-bottom flask. Dimethyl zinc, 50.00 ml of 1.0 M solution in heptane, is slowly added to the mixture via a gas-tight syringe. The starting ratio of zinc to silicon in the SAPO-34 is 9.00. The mixture is stirred at room temperature for 20 hr and centrifuged. The isolated solid is then stirred in 50 ml of anhydrous methanol for 4 hr at room temperature, centrifuged, and dried at 105° C. for one day. The solid is calcined at 600° C. for 3 hr before use and hereinafter referred to as Sample E.

COMPARATIVE EXAMPLE 7

Framework Incorporated Zinc SAPO-34

Framework incorporated zinc SAPO-34 is prepared hydrothermally by adding zinc acetate to the synthesis gel of SAPO-34 where triethylamine (TEA) is used as the template, following the procedures reported in EP 1143833 A1, which is fully incorporated herein by reference. The solid is hereinafter referred to as Sample F.

COMPARATIVE EXAMPLE 8

Cation Exchange with SAPO-34

3.3 g of SAPO-34 (Sample X) is refluxed with 0.86 g of $Zn(NO_3)_2.6H_2O$ in 35 ml of distilled water for 4 hr. The mixture is filtered and dried at 105° C. overnight. The solid is hereinafter referred to as Sample G.

COMPARATIVE EXAMPLE 9

Cation Exchange with SAPO-34

4.0 g of calcined SAPO-34 (Sample Y) is refluxed with 1.00 g of $Zn(NO_3)_2.6H_2O$ in 50 ml of distilled water for 4 hr. The mixture is filtered and dried at 105° C. overnight. The solid is hereinafter referred to as Sample H.

COMPARATIVE EXAMPLE 10

SAPO-34 Impregnation Via Incipient Wetness 4.0 g of SAPO-34 (Sample X) is slowly wetted with a solution of 0.22 g of $Zn(NO_3)_2 \cdot 6H_2O$ dissolved in 2.0 ml of de-ionized water. The wet mixture is dried at 105° C. overnight. The solid is hereinafter referred to as Sample I.

COMPARATIVE EXAMPLE 11

SAPO-34 Impregnation Via Incipient Wetness 4.0 g of SAPO-34 (Sample X), is slowly wetted with a solution of 0.52 g of $Zn(NO_3)_2 \cdot 6H_2O$ dissolved in 2.0 ml of de-ionized water. The wet mixture is dried at 105° C. overnight. The solid is hereinafter referred to as Sample J.

EXAMPLE 12

Methylmagnesium Bromide Treatment of SAPO-34

Under an $N_2$ atmosphere, 7.0 g of SAPO-34 (Sample Y) is placed in a 250-ml schlenk flask and chilled with an ice/acetone bath. A volume of 100 ml methylmagnesium bromide solution (0.7 M in 3/1 toluene/tetrahydrofuran (THF)) is cannulated into the flask. The mixture is allowed to warm up to room temperature and stirred at room temperature for 21 hr. The mixture is then filtered under $N_2$, washed with pentane, followed by ether, and dried under vacuum for 4 hr. The dry powder is stirred with 50 ml of anhydrous methanol for 4 hr and centrifuged. The solid is dried under vacuum overnight and calcined at 600° C. for 3 hr before use and hereinafter referred to as Sample K.

EXAMPLE 13

Dimethyl Zinc Treatment for SAPO-34

Under an $N_2$ atmosphere, 23.2 g of SAPO-34 (Sample Y) is suspended in 200 ml of anhydrous heptane in a 500-ml round-bottom flask. Dimethyl zinc, 7.0 ml of 1.0 M solution in heptane, is slowly added to the mixture via a gas-tight syringe. The starting ratio of zinc to silicon in the SAPO-34 is 0.25. The mixture is stirred at room temperature for 20 hr and centrifuged. The isolated solid is dried at 105° C. for one day and hereinafter referred to as Sample L.

EXAMPLE 14

Repetitive Low Dose Dimethyl Zinc Treatment for SAPO-34

Under an $N_2$ atmosphere, 15.4 g of Sample L is suspended in 150 ml of anhydrous heptane in a 500-ml round-bottom flask. Dimethyl zinc, 5.0 ml of 1.0 M solution in heptane, is slowly added to the mixture via a gas-tight syringe to bring the total starting ratio of zinc to silicon in the SAPO-34 to 0.5. The mixture is stirred at room temperature for 20 hr and centrifuged. The isolated solid is dried at 105° C. for one day and hereinafter referred to as Sample M.

EXAMPLE 15

Repetitive Low Dose Dimethyl Zinc Treatment for SAPO-34

Under an $N_2$ atmosphere, 9.7 g of Sample M is suspended in 100 ml of anhydrous heptane in a 250-ml round-bottom flask. Dimethyl zinc, 3.5 ml of 1.0 M solution in heptane, is slowly added to the mixture via a gas-tight syringe to bring the total starting ratio of zinc to silicon in the SAPO-34 to 0.75. The mixture is stirred at room temperature for 20 hr and centrifuged. The isolated solid is dried at 105° C. for one day and hereinafter referred to as Sample N.

EXAMPLE 16

Repetitive Low Dose Dimethyl Zinc Treatment for SAPO-34

Under an $N_2$ atmosphere, 5.2 g of Sample N is suspended in 60 ml of anhydrous heptane in a 250-ml round-bottom flask. Dimethyl zinc, 2.0 ml of 1.0 M solution in heptane, is slowly added to the mixture via a gas-tight syringe to bring the total starting ratio of zinc to silicon in the SAPO-34 to 1.0. The mixture is stirred at room temperature for 20 hr and centrifuged. The isolated solid is dried at 105° C. for one day and hereinafter referred to as Sample O.

EXAMPLE 17

Methane Formation During Dimethyl Zinc Treatment of SAPO-34

Under an $N_2$ atmosphere, 1.2 g of Sample Y is placed in a 50-ml round bottom flask and is evacuated under vacuum. Anhydrous heptane (24 ml) is added. The mixture is stirred under $N_2$, and 1.6 ml of dimethyl zinc solution (1.0 M in heptane) is added via a gas-tight syringe. The level of methane in the head space of the flask is analyzed by gas chromatography (GC) in order to follow the reaction.

FIG. 1 shows the evolution of methane with time after dimethyl zinc is added to SAPO-34. The Y-axis is the GC peak area ratio of methane vs. the solvent heptane ($A_{CH_4}/A_{C_7H_{16}}$). It is believed that if dimethyl zinc reacts mostly with the exterior acid sites of SAPO-34 and inadvertent moisture, immediate release of methane will result and the level of methane will rapidly reach its maximum. As shown in FIG. 1, it takes more than three hours for methane to reach its maximum level, indicating that dimethyl zinc diffuses inside the cage of SAPO-34 and reacts mostly with the interior acid sites.

The reaction is stopped and the solid isolated after $A_{CH_4}/A_{C_7H_{16}}$ has reached its maximum. The Zn/Si atomic ratio in the isolated solid is 0.73 as determined by elemental analysis (see Example 19 below).

EXAMPLE 18

Methane Formation During Methylmagnesium Bromide Treatment of SAPO-34

Under an $N_2$ atmosphere, 1.2 g of Sample Y is suspended in 30 ml of a 3/1 mixture of anhydrous toluene/anhydrous tetrahydrofuran in a 50-ml round bottom flask. A volume of 1.4 ml of methylmagnesium bromide solution (1.4 M in 3/1 toluene/THF) is added to the mixture via a gas tight syringe. The level of methane in the head space of the flask is analyzed by gas chromatography (GC) in order to follow the reaction.

FIG. 2 shows the evolution of methane with time after methylmagnesium bromide is added to SAPO-34. The Y-axis is the GC peak area ratio of methane vs. the solvent tetrahydrofuran ($A_{CH_4}/A_{THF}$). It is believed that if methylmagnesium bromide reacts mostly with the exterior acid sites of SAPO-34 and inadvertent moisture, immediate release of methane will result and the level of methane will rapidly reach its maximum. As shown in FIG. 2, it takes about two hours for methane level to reach its maximum, indicating that methylmagnesium bromide diffuses inside the cage of SAPO-34 and reacts with the interior acid sites.

The reaction is stopped and the solid isolated after $A_{CH_4}/A_{THF}$ has reached its maximum. The Mg/Si atomic ratio in the isolated solid is 0.43 as determined by elemental analysis (see Example 19 below).

EXAMPLE 19

Elemental Compositions of Modified SAPO-34

Elemental compositions of modified SAPO-34 samples are analyzed by Inductively Coupled Plasma/Atomic Emission Spectroscopy (ICP/AES) and the results are listed below in Table 1 (Samples A–J). Clearly, the amount of zinc incorporated in SAPO-34 can be controlled by varying the reaction stoichiometry between dimethyl zinc and SAPO-34 in Samples A–E. Similarly, the amount of zinc can also be controlled in the impregnated Samples I and J by varying the amount of zinc nitrate used. In contrast, the amount of zinc incorporated is limited in the cation-exchanged Samples G and H.

EXAMPLE 20

Methanol Uptake of Modified SAPO-34

Methanol uptake (expressed as weight percentage of methanol adsorbed by the molecular sieve) is measured gravimetrically and the results are listed below in Table 2. Clearly, samples of SAPO-34 modified with dimethyl zinc or methylmagnesium bromide have reduced methanol uptake, consistent with reduced cage volume after modification.

EXAMPLE 21

MAS $^1$H NMR Measurement of Modified SAPO-34

The Brønsted acid site density of the modified materials is measured by Magic Angle Spinning proton NMR spectroscopy (MAS $^1$H NMR). The $^1$H MAS NMR spectra are obtained on a Bruker AMX360 (360.13 MHz for $^1$H) wide bore spectrometer with a 4-mm (o.d.) MAS probe using 10-kHz spinning, 3.0 ms 90° pulses, a 30 s pulse delay, and 32 scans were collected. The absolute amount of $^1$H in each sample is determined by directly comparing the experimental spectral area relative to that of an external quantification standard and weight normalized. The external standards and the samples are run back-to-back under identical conditions to minimize any effects due to the spectrometer instability. The external quantification standard used is octakis (trimethylsiloxy)silesquioxane, more commonly known as Q8M8. Q8M8 is a solid at room temperature, has similar tuning characteristics to silicoaluminophosphates, and has a single peak at about 0.3 ppm from tetramethylsilane (TMS). It is commercially available from Strem Chemicals (CAS No. 51777-38-9). Measurements done in quadruplicate on similar systems give a standard deviation of <4% for this methodology. The results for Samples L–O as well as those for comparative Samples F and H are shown in FIG. 3.

FIG. 3 shows that: 1) the Brønsted acid site (3.7 ppm) density decreases proportionally with increasing amount of zinc incorporation, a result of increasing degree of dimethyl zinc modification; and 2) a new peak (1.0 ppm) appears in the dimethyl zinc modified samples, which grows proportionally with increasing amount of zinc incorporation. The data are summarized below in Table 3.

In contrast, the peak around 1 ppm is not seen in either Sample F (framework incorporated zinc SAPO-34) or Sample H ($Zn^{2+}$ cation exchanged SAPO-34). Therefore MAS $^1$H NMR clearly shows the structural difference between dimethyl zinc modified SAPO-34 and other zinc-containing SAPO-34 wherein zinc is introduced via other methods.

EXAMPLE 22

Conversion of Methanol to Olefins (MTO)

Conversion of methanol to olefins is carried out in a continuous, tubular, stainless steel reactor (i.d.=0.4 cm; l=13 cm). An amount of 0.025–0.05 g of the calcined and pelletized (40–80 mesh) catalyst is loaded along with quartz granules in the center zone of the tube. The catalyst is heated to 450° C. in flowing nitrogen prior to the MTO reaction. The reaction temperature is either 400° C. or 450° C. as indicated in the Tables below. In all MTO runs, the pressure of the reactor is maintained at 15 psig with the use of a back-pressure regulator. Methanol is fed to the reactor as saturated vapor by bubbling nitrogen through a reservoir of methanol held at 20° C. The effluent from the reactor is analyzed with an HP5890 Series II Plus Gas Chromatograph with a flame ionization detector (FID). In order to compare selectivity of different catalysts, the weight hourly space velocity (WHSV) is adjusted to keep conversion level similar (90–95%). Selectivity is chosen at the conversion level shown. Catalyst lifetime is defined as the amount of methanol fed through the catalyst from the beginning of reaction to the point where about 50% oxygenates are converted. The results are shown below in Tables 4–6.

Shown in Table 4 below are the MTO product selectivity (400° C.) for Samples A, D and K modified according to the method of the present invention. Results for Sample Y are also shown for comparison.

Table 5 below shows MTO product selectivity (450° C.) for Samples B and C modified according to the present invention and comparative Samples F (framework incorporated) and G (cation exchange with template). Results for Sample Y are also shown for comparison.

MTO product selectivity (450° C.) is shown in Table 6 below for comparative Samples H (cation exchange without template), I (impregnation) and J (impregnation). Results for Sample Y are also shown for comparison.

EXAMPLE 23

Conversion of Methanol to Olefins (MTO) at High Pressure

Samples of dimethyl zinc modified SAPO-34 (Sample L–O) have also been tested for MTO reactions in a high-pressure micro-reactor. Typical conditions are: 25 psig, 475° C., and WHSV=100 h$^{-1}$. The results are listed in Table 7 below. Selectivity shown is the integrated selectivity through the course of the reaction. Catalyst lifetime is defined as the total amount of methanol converted per gram of catalyst from beginning of reaction to a conversion level of about 10%.

The MTO performance results clearly indicate that the organometallic modification results in an increase in selectivity toward ethylene (Samples A–D, L–O). Total ethylene and propylene selectivity also increases with organometallic treatment (Samples A–D).

Framework incorporated ZnSAPO-34 (Sample F) with similar amount of zinc does not show significant advantage in terms of olefin selectivity. In addition, it is far more difficult to regenerate framework zinc than to replace intra-/inter-cage zinc using dimethyl zinc. Cation exchanged SAPO-34 (Samples G and H) that starts with either calcined (without template) or uncalcined (with template) SAPO-34 does not show significant increase in ethylene selectivity either. Impregnation methods such as incipient wetness (Samples I and J) can achieve similar level of zinc to those of dimethyl zinc modification, however the selectivity toward ethylene does not increase as significantly compared to those of the organometallic modification according to the method of the present invention.

EXAMPLE 24

Conversion of Methanol to Olefins (MTO) for Regenerated Catalysts

Deactivated catalyst (Sample B) after methanol-to-olefins conversion according to Example 22 above is regenerated in-situ by passing air through the reactor at 550° C. for two hours. MTO conversion is then resumed under identical conditions used for the fresh catalyst. The results are shown in FIG. 4. Little or no change in performance is observed, indicating good hydrothermal stability for dimethyl zinc modified SAPO-34 (Sample B).

TABLE 1

Elemental composition of modified SAPO-34

| Sample | Metal (M) | Metal loading incorporated (wt. %) | Composition (atomic ratio) | | | | |
|---|---|---|---|---|---|---|---|
| | | | M | Si | Al | P | M/Si |
| Y | None | 0.0 | 0 | 0.142 | 1 | 0.768 | 0 |
| A | Zn | 2.6 | 0.049 | 0.14 | 1 | 0.776 | 0.35 |
| B | Zn | 1.5 | 0.028 | 0.138 | 1 | 0.745 | 0.21 |
| C | Zn | 3.5 | 0.066 | 0.141 | 1 | 0.757 | 0.47 |
| D | Zn | 9.6 | 0.2 | 0.143 | 1 | 0.755 | 1.4 |
| E | Zn | 18.7 | 0.44 | 0.135 | 1 | 0.72 | 3.3 |
| F | Zn | 2.5 | 0.05 | 0.106 | 1 | 1.02 | 0.47 |
| G | Zn | 0.3 | 0.006 | 0.134 | 1 | 0.748 | 0.04 |
| H | Zn | 0.28 | 0.0052 | 0.138 | 1 | 0.751 | 0.04 |
| I | Zn | 1.2 | 0.022 | 0.143 | 1 | 0.767 | 0.15 |
| J | Zn | 3.5 | 0.067 | 0.143 | 1 | 0.763 | 0.47 |
| K | Mg | 1.9 | 0.094 | 0.138 | 1 | 0.748 | 0.68 |

TABLE 2

Methanol uptake of modified SAPO-34

| Sample | Metal (M) incorporated | Methanol uptake (wt %) |
|---|---|---|
| Y | None | 25 |
| A | Zn | 22 |
| D | Zn | 15 |
| E | Zn | 6 |
| G | Zn | 20 |
| K | Mg | 22 |

TABLE 3

MAS $^1$H NMR of dimethyl zinc modified SAPO-34

| Sample | Composition | | | | | Zn loading (wt. %) | Brønsted acid site (3.7 ppm) density (mmole/g) | New peak (1.0 ppm) density (mmole/g) |
|---|---|---|---|---|---|---|---|---|
| | Zn | Si | Al | P | Zn/Si | | | |
| Y | 0 | 0.142 | 1 | 0.768 | 0 | 0.0 | 1.37 | 0 |
| L | 0.03 | 0.149 | 1 | 0.789 | 0.20 | 1.6 | 1.08 | 0.18 |
| M | 0.062 | 0.149 | 1 | 0.781 | 0.42 | 3.2 | 0.88 | 0.26 |
| N | 0.096 | 0.156 | 1 | 0.794 | 0.61 | 4.9 | 0.74 | 0.35 |
| O | 0.152 | 0.174 | 1 | 0.779 | 0.87 | 7.4 | 0.54 | 0.28 |

TABLE 4

MTO performance (400° C.) for ZnMe$_2$ and MeMgBr modified SAPO-34

| Sample | | Y | A | D | K |
|---|---|---|---|---|---|
| M/Si ratio | | 0 | 0.35 | 1.4 | 0.68 |
| Modification | | None | ZnMe$_2$ | ZnMe$_2$ | MeMgBr |
| WHSV (h$^{-1}$) | | 20 | 15 | 2.5 | 10 |
| Conversion (%) | | 97 | 94.2 | 92 | 95 |
| Lifetime (g MeOH fed/g catalyst) | | 16 | 11 | 1.3 | 11.5 |
| Selectivity (wt %) | C$_2^=$ | 33.3 | 37.3 | 49.4 | 32.4 |
| | C$_3^=$ | 44.9 | 41.8 | 33.5 | 45.4 |
| | C$_4^=$ | 13.9 | 10.2 | 7 | 13.3 |
| | CH$_4$ | 0.55 | 1.67 | 3.9 | 0.77 |
| | C$_2$ | 0.82 | 0.97 | 0.26 | 1.39 |
| | C$_3$ | 1.62 | 1.69 | 0.97 | 1.82 |
| | C$_4$ | 0.59 | 0.48 | 0.23 | 0.87 |
| | C$_5$–C$_6$ | 4.6 | 5.92 | 4.8 | 4.5 |
| C$_2^=$/C$_3^=$ | | 0.75 | 0.9 | 1.5 | 0.71 |
| C$_2^=$ + C$_3^=$ | | 78.2 | 79.1 | 82.9 | 77.8 |

TABLE 5

MTO performance (450° C.) for SAPO-34 modified with zinc according to different methods.

| Sample | | Y | B | C | F | G |
|---|---|---|---|---|---|---|
| Zn/Si ratio | | 0 | 0.2 | 0.47 | 0.5 | 0.045 |
| Modification | | None | ZnMe$_2$ | ZnMe$_2$ | Framework incorporated | Cation exchange |
| WHSV (h$^{-1}$) | | 20 | 30 | 15 | 25 | 30 |
| Conversion (%) | | 90 | 92 | 95 | 91 | 90 |
| Lifetime (g MeOH fed/g catalyst) | | 19 | 7 | 5 | 8 | 18 |
| Selectivity (wt %) | C$_2^=$ | 38.5 | 44.5 | 52 | 38.9 | 41.9 |
| | C$_3^=$ | 38.3 | 37.2 | 29.2 | 38.2 | 37.2 |
| | C$_4^=$ | 11.5 | 8.3 | 7.2 | 11.8 | 10.1 |
| | CH$_4$ | 1.1 | 3 | 7.4 | 4 | 2.2 |
| | C$_2$ | 0.9 | 1.1 | 0.5 | 0.9 | 0.3 |
| | C$_3$ | 0.8 | 1.0 | 0.5 | 1.2 | 0.7 |
| | C$_4$ | 0.2 | 0.2 | 0.05 | 0.2 | 0.2 |
| | C$_5$–C$_6$ | 8.6 | 4.6 | 3.1 | 4.8 | 7.2 |
| C$_2^=$/C$_3^=$ | | 1 | 1.2 | 1.8 | 1 | 1.1 |
| C$_2^{=}$ + C$_3^=$ (wt %) | | 76.8 | 81.7 | 81.2 | 77.1 | 79.2 |

TABLE 6

MTO performance (450° C.) for SAPO-34 modified with zinc according to different methods.

| Sample | Y | H | I | J |
|---|---|---|---|---|
| Zn/Si ratio | 0 | 0.038 | 0.15 | 0.47 |
| Modification | None | Cation exchange (w/o template) | Impregnation | Impregnation |
| WHSV ($h^{-1}$) | 30 | 60 | 30 | 30 |
| Conversion (%) | 95 | 96 | 95 | 94 |
| Lifetime (g MeOH fed/g catalyst) | 25 | 12 | 14 | 7 |
| Selectivity $C_2^=$ | 41 | 35.67 | 45.6 | 48.6 |
| (wt %) $C_3^=$ | 36.9 | 41.81 | 36.1 | 34.6 |
| $C_4^=$ | 10.8 | 12.1 | 9.4 | 8.1 |
| $CH_4$ | 2.2 | 3.36 | 1.8 | 3.4 |
| $C_2$ | 0.3 | 0.31 | 0.4 | 0.35 |
| $C_3$ | 0.75 | 1.05 | 0.6 | 0.45 |
| $C_4$ | 0.14 | 0.14 | 0.12 | 0.1 |
| $C_5$–$C_6$ | 7.8 | 5.2 | 6 | 4.4 |
| $C_2^=/C_3^=$ | 1.1 | 0.85 | 1.26 | 1.4 |
| $C_2^= + C_3^=$ | 77.9 | 77.5 | 81.7 | 83.2 |

TABLE 7

MTO performance (25 psig, 475° C.) for SAPO-34 modified with zinc according to the present invention.

| Sample | Y | L | M | N | O |
|---|---|---|---|---|---|
| Zn/Si ratio | 0 | 0.20 | 0.42 | 0.61 | 0.87 |
| Modification | None | $ZnMe_2$ | $ZnMe_2$ | $ZnMe_2$ | $ZnMe_2$ |
| WHSV ($h^{-1}$) | 100 | 100 | 100 | 100 | 100 |
| Lifetime (g MeOH converted/g catalyst) | 14.3 | 14.6 | 6.34 | 2.4 | 2.1 |
| Selectivity $C_2^=$ | 35.8 | 37.6 | 36.87 | 34.04 | 32.84 |
| (wt %) $C_3^=$ | 40.8 | 38.1 | 37.35 | 33.04 | 33.33 |
| $C_4^=$ | 14.8 | 13.8 | 12.25 | 9.47 | 9.67 |
| $CH_4$ | 1.44 | 2.14 | 3.05 | 5.61 | 5.89 |
| $C_2$ | 0.71 | 0.73 | 0.91 | 1.9 | 1.84 |
| $C_3$ | 1.85 | 1.64 | 2.0 | 3.92 | 3.75 |
| $C_4$ | 0.0 | 0.02 | 0.15 | 0.49 | 0.42 |
| $C_5$–$C_6$ | 1.97 | 2.56 | 2.77 | 2.73 | 3.34 |
| $C_2^=/C_3^=$ | 0.88 | 0.99 | 0.99 | 1.03 | 0.99 |
| $C_2^{32} + C_3^=$(wt %) | 76.63 | 75.65 | 74.22 | 67.08 | 66.16 |

Having now fully described this invention, it will be appreciated by those skilled in the art that the invention can be performed within a wide range of parameters within what is claimed, without departing from the spirit and scope of the invention.

What is claimed:

1. A method for making an organometallic treated molecular sieve comprising:
   a) providing a molecular sieve having at least one hydroxyl group;
   b) contacting said molecular sieve with a solution comprising an organometallic compound and a non-proton donating solvent, wherein said organometallic compound comprises at least one metal selected from the group consisting of zinc, lithium, magnesium, gallium, germanium, and mixtures thereof, bound to at least one alkyl group; and
   c) separating the organometallic treated molecular sieve from the solution.

2. The method of claim 1, comprising calcining the molecular sieve prior to step b).

3. The method of claim 2, wherein said calcining is carried out at temperature of at least about 300° C. and most about 800° C.

4. The method of claim 3, wherein said calcining is carried out at temperature of at least about 450° C. and at most about 750° C.

5. The method of claim 4, wherein said calcining is carried out at temperature of at least about 550° C. and at most about 700° C.

6. The method of claim 2, wherein said calcining is carried out in the presence of oxygen.

7. The method of claim 2, wherein said calcining is carried out for a period of at least about 1 hour and at most about 24 hours.

8. The method of claim 7, wherein said calcining is carried out for a period of at least about 2 hours and at most about 12 hours.

9. The method of claim 8, wherein said calcining is carried out at for a period of at least about 2 hours and at most about 10 hours.

10. The method of claim 1, wherein step b) is carried out for a period of at least about 1 hour and at most about 10 hours.

11. The method of claim 10, wherein step b) is carried out for a period of at least about 2 hours and at most about 24 hours.

12. The method of claim 11, wherein step b) is carried out for a period of at least about 3 hours and at most about 0 hours.

13. The method of claim 1, wherein step b) is carried out with stirring.

14. The method of claim 1, wherein the metal is selected from the group consisting of Group 1 to Group 14 and mixtures thereof.

15. The method of claim 1, wherein said organometallic compound is selected from the group consisting of methyl lithium, butyl lithium, dimethyl zinc, diethyl zinc, ethylmagnesium bromide, methylmagnesium bromide, trimethyl gallium, triethyl gallium, tetraethyl gallium, tetramethyl gallium, and mixtures thereof.

16. The method of claim 15, wherein said organometallic compound is dimethyl zinc.

17. The method of claim 15, wherein said organometallic compound is methylmagnesium bromide.

18. The method of claim 1, said at least one alkyl group has from 1 to 20 carbon atoms.

19. The method of claim 18, wherein said at least one alkyl group has from 1 to 6 carbon atoms.

20. The method of claim 1, wherein said at least one alkyl group is linear.

21. The method of claim 1, wherein said organometallic compound in solution has a concentration of at least about 0.001 M and at most about 10 M.

22. The method of claim 1, wherein said organometallic compound in solution has a concentration of at least about 0.005 M arid at most about 5 M.

23. The method of claim 1, wherein the concentration of said organometallic compound in said solution is a 0.01 M to about 3 M.

24. The method of claim 1, wherein step b) is repeated.

25. The method of claim 1, wherein said non-proton donating solvent is selected from the group consisting of heptane, tetrahydrofuran, benzene, toluene, xylenes, diethyl ether and mixtures thereof.

26. The method of claim 1, wherein the amount of metal loading in the organometallic treated molecular sieve is at least about 0.05 % by wt. metal and at most about 20 % by wt. metal.

27. The method of claim 26, wherein the amount of metal loading in the organometallic treated molecular sieve is at least about 0.5 % by wt. metal and at most about 10 % by wt. metal.

28. The method of claim 27, wherein the amount of metal loading in the organometallic treated molecular sieve is at least about 1.0 % by wt. metal and at most about 8.0 % by wt. metal.

29. The method of claim 1, wherein the organometallic treated molecular sieve has a metal to silicon atomic from 0.001 to 3.0.

30. The method of claim 26, wherein the organometallic treated molecular sieve has a metal to silicon atomic ratio of from 0.01 to 2.5.

31. The method of claim 27 wherein the organometallic treated molecular sieve has a metal to silicon atom ratio of from 0.02 to 2.0.

32. The method of claim 1, said molecular sieve has an average pore opening of at least about 3 Angstroms and at most about 8 Angstrom a.

33. The method of claim 32, wherein said molecular sieve has an average pore opening of at least about 3.5 Angstroms and at most about 5.5 Angstroms.

34. The method of claim 33, in said molecular sieve has an average pore opening of at least about 3.8 Angstroms and at most about 4.2 Angstroms.

35. The method of claim 1, wherein the molecular sieve is an aluminosilicate molecular sieve.

36. The method of claim 35, wherein the aluminosilicate molecular sieve is selected from the group consisting of ZSM-5, ZSM-34, chabazite, erionite, and mixtures thereof.

37. An organometallic treated molecular sieve prepared by the method of claim 1.

38. A calcined, organometallic treated molecular sieve prepared by the method of claim 1.

39. The calcined, organometallic treated molecular sieve of claim 35, having a reduced cage volume from cage volume of the molecular sieve prior to step b), as measured by methanol uptake.

40. The calcined, calcined, treated molecular sieve of claim 35, having a reduced acidity from acidity of the molecular sieve prior to step b), as measured by MAS $^1$H NMR.

41. The calcined, dimethyl zinc treated SAPO-34 having signature peak at about δ=1.0 ppm, as measured by MAS $^1$H NMR.

42. A catalyst comprising a calcined, organometallic treated molecular sieve prepared by the method of claim 1 and a binder.

43. The catalyst of claim 42, wherein the binder is selected from the group consisting of alumina, aluminum chlorohydrol, clay, and mixtures thereof.

44. A method for making an organometallic treated molecular sieve comprising:
   a) providing a molecular sieve having at least one hydroxyl group;
   b) contacting said molecular sieve with a solution comprising an organometallic compound and a non-proton donating solvent, wherein said organometallic compound comprises at least one metal; and
   c) separating the organometallic treated molecular sieve from the solution, wherein said organometallic treated molecular sieve is calcined after step b).

45. The method of claim 44, wherein said calcining is carried out at a temperature of at least about 300° C. and at most about 800° C.

46. The method of claim 45, wherein said calcining is carried out at a temperature of at least about 450° C. and at most about 750° C.

47. The method of claim 46, wherein said calcining is carried out at a temperature of at least about 550° C. and at most about 750° C.

48. The method of claim 44, wherein said calcining is carried out in the presence of oxygen.

49. The method of claim 44, wherein said calcining is carried out for a period of at least about 1 hour and at most about 24 hours.

50. The method of claim 49, wherein said calcining is carried out for a period of at least about 2 hours and at most about 12 hours.

51. The method of claim 50, wherein said calcining is carried out for a period of at least about 3 hours and at most about 10 hours.

52. The method of claim 44, further comprising calcining both the molecular sieve prior to step b) and the organometallic treated molecular sieve after step b).

53. The method of claim 44, wherein step b) is carried out at a temperature of at least about −40° C. and at most about 200° C.

54. The method of claim 53, wherein step b) is carried out at a temperature of at least about −25° C. and at most about 150° C.

55. The method of claim 54, wherein step b) is carried out at a temperature of at least about 0° C. and at most 100° C.

56. A method for making an organometallic treated molecular sieve comprising:
   a) providing a silicoaluminophosphate molecular sieve having at least one hydroxyl group;
   b) contacting said silicoaluminophosphate molecular sieve with a solution comprising an organometallic compound and a non-protein donating solvent, wherein said organometallic compound comprises at least one metal bound to at least one alkyl group; and
   c) separating the organometallic treated silicoaluminophosphate molecular sieve from the solution.

57. The method of claim 56 wherein the silicoaluminophosphate molecular sieve is selected from the group consisting of SAPO-17, SAPO-18, SAPO-34, SAPO-35, SAPO-44, SAPO-47, SAPO-56 and mixtures thereof.

58. The method of claim 57, wherein the silicoaluminophosphate molecular sieve is selected from the group consisting of SAPO-18, SAPO-34, intergrowths of SAPO-18 and SAPO-34 and mixtures thereof.

59. The method of claim 58, in the silicoaluminophosphate molecular sieve is SAPO-34.

* * * * *